(12) United States Patent
Sun et al.

(10) Patent No.: US 11,279,079 B2
(45) Date of Patent: Mar. 22, 2022

(54) CELL ELECTROCHEMICAL SENSOR BASED ON 3D PRINTING TECHNOLOGY AND APPLICATION THEREOF

(71) Applicant: Jiangnan University, Wuxi (CN)

(72) Inventors: Xiulan Sun, Wuxi (CN); Jiadi Sun, Wuxi (CN); Jian Ji, Wuxi (CN); Yinzhi Zhang, Wuxi (CN); Kaimin Wei, Wuxi (CN)

(73) Assignee: Jiangnan University, Wuxi (CN)

( * ) Notice: Subject to any disclaimer, the term of this patent is extended or adjusted under 35 U.S.C. 154(b) by 0 days.

(21) Appl. No.: 17/034,261

(22) Filed: Sep. 28, 2020

(65) Prior Publication Data

US 2021/0023770 A1    Jan. 28, 2021

(30) Foreign Application Priority Data

Apr. 1, 2020  (CN) .......................... 202010249330.X

(51) Int. Cl.
*G01N 27/327*    (2006.01)
*B29C 64/106*    (2017.01)
(Continued)

(52) U.S. Cl.
CPC ............ *B29C 64/106* (2017.08); *B33Y 10/00* (2014.12); *B33Y 80/00* (2014.12);
(Continued)

(58) Field of Classification Search
None
See application file for complete search history.

(56) References Cited

U.S. PATENT DOCUMENTS 7,939,003 B2 * 5/2011 Bonassar ............... B33Y 30/00
264/308

FOREIGN PATENT DOCUMENTS

CN    102944598 A    2/2013
CN    203178279 U    9/2013
(Continued)

OTHER PUBLICATIONS

Donglei Jiang et al., "A novel electrochemical mast cell-based paper biosensor for the rapid detection of mil allergen casein", Biosensors and Bioelectronics 130 (2019)299-306, Jan. 30, 2019 (Year: 2019).*
(Continued)

*Primary Examiner* — Monica A Huson
*Assistant Examiner* — Kelsey C Grace
(74) *Attorney, Agent, or Firm* — IPro, PLLC

(57) ABSTRACT

The disclosure relates to a cell electrochemical sensor based on a 3D printing technology and application thereof and belongs to the technical field of electrochemical sensors and toxin detection. The cell electrochemical sensor of the disclosure is constructed based on a 3D printing technology, and the construction method comprises the following steps: precisely depositing a cell/carbon nanofiber/GelMA composite hydrogel on a working electrode of a screen-printed carbon electrode through 3D printing, and carrying out curing to obtain the cell electrochemical sensor. The disclosure constructs a cell electrochemical sensor with a three-dimensional cell growth environment and rapid and sensitive response. The cell electrochemical sensor constructed by the disclosure can be used for quickly and effectively determining the combined effect type and effect degree of deoxynivalenol family toxins by combining an electrochemical impedance method and a combination index method.

6 Claims, 9 Drawing Sheets

(51) Int. Cl.
  *B33Y 10/00*   (2015.01)
  *B33Y 80/00*   (2015.01)
  *G01N 33/50*   (2006.01)
  *B29K 105/12*  (2006.01)
  *B29K 307/04*  (2006.01)

(52) U.S. Cl.
  CPC ..... *G01N 27/3278* (2013.01); *G01N 33/5014* (2013.01); *B29K 2089/00* (2013.01); *B29K 2105/124* (2013.01); *B29K 2307/04* (2013.01)

(56) References Cited

FOREIGN PATENT DOCUMENTS

| CN | 106645344 A | 5/2017 |
|----|-------------|--------|
| CN | 107219274 A | 9/2017 |

OTHER PUBLICATIONS

Thomas Robert Heinrich Buch, et al., "Functional expression of the transient receptor potential channel TRPA1, a sensor for toxic lung inhalants, in pulmonary epithelial cells", Chemico-Biological Interactions, vol. 206, Issue 3, Dec. 5, 2013, pp. 462-471 (Year: 2013).*

Ddonglei Jiang et. al., "A novel electrochemical mast cell-based paper biosensor for the rapid detection of mil allergen casein", Biosensors and Bioelectronics 130 (2019)299-306, Jan. 30, 2019.

Su Ryon Shin, et. al., "Carbon nanotube reinforced hybrid microgels as scaffold martials for cell encapsulation", ACS Nano, vol. 6 No. 1, 362-372, Nov. 26, 2011.

* cited by examiner

CELL ELECTROCHEMICAL SENSOR BASED ON 3D PRINTING TECHNOLOGY AND APPLICATION THEREOF

TECHNICAL FIELD

The disclosure relates to a cell electrochemical sensor based on a 3D printing technology and application thereof and belongs to the technical field of electrochemical sensors and toxin detection.

BACKGROUND 3D printing technology is a computer-aided technology which produces engineering tissue in a mechanized, organized and optimized way, can assemble tissue by precisely positioning biological materials and living cells layer by layer, and has spatial control capabilities. 3D printing can be used not only to make basic arrays, but also to develop more complex arrays by setting different stay times or repeating specific G codes without making special molds or masks, which enables bioprinting of three-dimensional tumor array chips meeting a series of specific drug screening requirements for rapid on-demand drug screening.

For a long time, the pollution problem of mycotoxins in food and feed has always been serious, the global food and feed loss caused by fungal pollution accounts for 20%-30% of the total output, the deoxynivalenol-family mycotoxins are the mycotoxins with the highest detection rate in the northern hemisphere, the most serious one is deoxynivalenol (DON), and the main polluted crops comprise wheat, corn and the like. DON is heat-resistant, acid-resistant and storage-resistant. The structure of DON cannot be destroyed by general heat treatment processing methods, and after humans and animals eat food containing DON, different degrees of toxic reactions, such as vomiting and loss of appetite can be caused. In addition to DON, acetylated derivatives (such as 3-ADON, 15-ADON) of DON are often detected in grains such as wheat and corn. Both 3-ADON and 15-ADON belong to the deoxynivalenol-family mycotoxins. It is shown through in-vivo experiments in pigs that 3-ADON can be quickly converted into DON in blood; data shows that acetylated DON can be absorbed by intestinal tissue faster and is considered to be more toxic. Based on the high toxicity and high detection rate of DON, countries and regions have established clear limit standards for DON. The EU defines the limit standard of DON in different foods to be 200-1750 μg/kg. China defines in the national standard G2762-2017 that DON in grains and products thereof shall not exceed 1000 μg/kg. Current researches on the toxicity of toxins often focus on a single toxin, and there is a lack of comprehensive studies on the types and mechanisms of combined effects of mycotoxins.

Current toxicity evaluation methods mainly rely on two-dimensional cell experiments and animal experiments. Two-dimensional cell experiment methods have a low cost, a short cycle and certain homology with the body, but two-dimensional cell culture environments have greater differences from human body environments. Although results of animal toxicology experiments can truly, comprehensively and systematically reflect the effects of drugs on the body, there are disadvantages of high cost, long cycle, unsatisfactory repeatability, etc.

With the development and progress of science and technology, a variety of new technologies and methods combining traditional cell and sensor technologies provide more new methods for the study of toxicity mechanisms. In the construction of cell sensors, cells serving as receptors are immobilized to the interface. When the cells are stimulated by external drugs, changes in cell physiological activity can be caused. These changes can be converted into photoelectric signals. The magnitude of the signal changes can be used in qualitative and quantitative analysis of drug stimulation of cells. Currently, the patent (CN 107219274 B) discloses a preparation method of a cell electrochemical sensor for analyzing the combined toxicity of mycotoxins. The method specifically comprises the steps of immobilizing laminin to the surface of an electrode, then inoculating the electrode surface with cells, and dropwise adding rat tail collagen to form a 3D complex to immobilize the cells to obtain the cell sensor. The sensor prepared in this way may have problems of uneven distribution and low detection precision.

SUMMARY

In order to solve at least one of the problems above, the disclosure provides a construction method of a cell electrochemical sensor based on a 3D printing technology and application of the sensor in combined toxicity evaluation of deoxynivalenol-family mycotoxins. The disclosure uses the combination of 3D printing and an electrochemical cell sensor to construct a three-dimensional lung adenocarcinoma epithelial cell culture system which is reliable, easy to operate and high in reproducibility. The impedance value is measured by an electrochemical AC impedance method to judge the damage conditions of cells after the cells are stimulated by toxins so as to quickly and effectively evaluate the cytotoxicity of mycotoxins. The combination index method (CI) is combined to analyze the combined toxicity of two or more toxins and determine the combined effect type.

The first objective of the disclosure is to provide a method for preparing a cell electrochemical sensor. The cell electrochemical sensor is constructed based on a 3D printing technology. The construction method comprises the following steps:

(1) preparing a cell/carbon nanofiber/GelMA composite hydrogel: a carbon nanofiber solution is added into a gelatin methacryloyl (GelMA) solution for uniform mixing to obtain a carbon nanofiber/GelMA composite solution; then cells are uniformly mixed with the carbon nanofiber/GelMA composite solution to obtain the cell/carbon nanofiber/GeMA composite hydrogel; and (2) precisely depositing the cell/carbon nanofiber/GelMA composite hydrogel on a working electrode of a screen-printed carbon electrode through 3D printing, and carrying out curing to obtain the cell electrochemical sensor.

In an embodiment of the disclosure, the final concentration of GelMA in the cell/carbon nanofiber/GelMA composite hydrogel is 5-15%, preferably 5-7.5%.

In an embodiment of the disclosure, the final concentration of cells in the cell/carbon nanofiber/GelMA composite hydrogel is $1 \times 10^6$-$1 \times 10^7$/mL.

In an embodiment of the disclosure, the final concentration of carbon nanofibers in the cell/carbon nanofiber/GelMA composite hydrogel is 0.5-1 mg/mL.

In an embodiment of the disclosure, the carbon nanofibers are purchased from Xianfeng Nano, the model is XFM60, the diameter is 200-600 nm, and the length is 5-50 m.

In an embodiment of the disclosure, the cells are lung adenocarcinoma epithelial cells A549.

In an embodiment of the disclosure, 3D printing specifically comprises: pouring the cell/carbon nanofiber/GelMA composite hydrogel into a printing syringe, setting an initial needle position, a syringe temperature, a working platform temperature, an extrusion pressure, a graphic size, a graphic layer number and a nozzle walking speed, then precisely depositing the composite hydrogel on the working electrode of the screen-printed carbon electrode through 3D printing, and curing the composite hydrogel under a portable curing light source.

In an embodiment of the disclosure, a three-dimensional structure model of 3D printing is a circle with the diameter of 3 mm, the printing layer number is 1, and the printing layer height is 0.3 mm; the printing cylinder temperature is 23-27° C., the platform temperature is 1-5° C., the needle inner diameter is 0.26 mm, the extrusion pressure is 0.08-0.2 Mpa, and the nozzle walking speed is 180-300 mm/min.

In an embodiment of the disclosure, a bioprinted cell and hydrogel complex is irradiated with a portable curing light source with the wavelength of 405 nm for 10-20 seconds for curing.

In an embodiment of the disclosure, a preparation method of the cell/carbon nanofiber/GelMA composite hydrogel specifically comprises:

(1) preparation of a gelatin methacryloyl (GelMA) solution: an LAP initiator is added into a DMEM cell culture medium for well mixing and dissolving, and then a GeMA material is added into the dissolved standard initiator solution for dissolving in a water bath in the dark to obtain the GelMA solution; and (2) preparation of the cell/carbon nanofiber/GelMA composite hydrogel: a carbon nanofiber solution is added into the gelatin methacryloyl (GelMA) solution for uniform mixing to obtain a carbon nanofiber/GelMA composite solution; then cells are uniformly mixed with the carbon nanofiber/GelMA composite solution to obtain the cell/carbon nanofiber/GeMA composite hydrogel.

In an embodiment of the disclosure, the LAP standard initiator solution in step (1) is prepared with a DMEM cell culture medium, the mass concentration of the LAP standard initiator solution is 0.5%, the dissolution temperature is 50-60° C., and the dissolution time is 15-30 minutes; the mass concentration of the GeMA solution is 5%-15%, the dissolution temperature is 50-60° C., and the dissolution time is 15-30 minutes; after being completely dissolved, the GelMA solution is filtered by a 0.22 μm sterile filter membrane for sterilization.

In an embodiment of the disclosure, a preparation method of the carbon nanofiber solution in step (2) comprises: adding a certain amount of carbon nanofibers into a phosphate buffer solution (PBS) to make the concentration of carbon nanofibers reach 1-2 mg/mL, and carrying out ultrasonic treatment for 2 hours to obtain the carbon nanofiber solution.

In an embodiment of the disclosure, in step (2), the final concentration of cells is adjusted to be $1 \times 10^6$-$1 \times 10^7$/mL, and the final concentration of carbon nanofibers is 0.5-1 mg/mL.

In an embodiment of the disclosure, after the carbon nanofiber solution is prepared and the screen-printed carbon electrode is electroplated with gold nanoparticles, both the carbon nanofiber solution and the screen-printed carbon electrode need to be placed under an ultraviolet light for irradiation for 2 hours or above for sterilization treatment.

In an embodiment of the disclosure, the screen-printed carbon electrode is a modified screen-printed carbon electrode obtained by modifying and electroplating the screen-printed carbon electrode with gold nanoparticles.

In an embodiment of the disclosure, the gold nanoparticles are prepared from 1 mL of 1% chloroauric acid, 1 mL of 1 mmol/L sulfuric acid solution and 8 mL of ultrapure water. The gold nanoparticles are deposited on the screen-printed carbon electrode by an electroplating method, the electroplating voltage is −0.2-0.4 V, and the electroplating time is 120-160 seconds.

The second objective of the disclosure is a cell electrochemical sensor prepared by the method of the disclosure, and the cell/carbon nanofiber/GeMA composite hydrogel is immobilized on the surface of the working electrode in the cell electrochemical sensor.

In an embodiment of the disclosure, the final concentration of GelMA in the cell/carbon nanofiber/GelMA composite hydrogel is 5-15%, preferably 5-7.5%.

In an embodiment of the disclosure, the final concentration of cells in the cell/carbon nanofiber/GelMA composite hydrogel is $1 \times 10^6$-$1 \times 10^7$/mL.

In an embodiment of the disclosure, the final concentration of carbon nanofibers in the cell/carbon nanofiber/GelMA composite hydrogel is 0.5-1 mg/mL.

The third objective of the disclosure is to provide a method for evaluating the toxicity of deoxynivalenol-family mycotoxins by using the cell electrochemical sensor of the disclosure. The method is as follows: one toxin is used to stimulate the cell sensor alone or two or more toxins are combined to act on the cell sensor, and then the electrochemical AC impedance method and the combination index method are used to analyze the cytotoxicity or the combined effect type.

In an embodiment of the disclosure, the cell sensor needs to be incubated before application, and specific operations comprise: dropping a DMEM cell culture medium at a working electrode of a screen-printed carbon electrode to ensure that the culture medium can cover a cell/carbon nanofiber/GelMA complex on the working electrode to provide cells with nutrients needed for growth, and then placing the working electrode in an incubator with the carbon dioxide concentration of 5% and the humidity of 95% for incubation at 37° C. for 6-12 hours; after incubation, removing the original culture medium on the working electrode, diluting toxin standard substances with the DMEM cell culture medium into gradient concentration solutions, dropping the gradient concentration solutions on the working electrode printed with cells, and then carrying out electrochemical detection after placing the working electrode in the incubator for effect for 24 hours.

In an embodiment of the disclosure, the deoxynivalenol-family mycotoxins are one or two of deoxynivalenol (DON) and 15-acetyl-deoxynivalenol (15-ADON).

In an embodiment of the disclosure, the method uses a modified screen-printed carbon electrode as a sensing interface, a PET material is used as a substrate, the working electrode is composed of carbon, the reference electrode is composed of silver/silver chloride, the counter electrode is composed of carbon, electrochemical detection adopts electrochemical impedance spectroscopy (EIS) to test electrical signal changes of cells stimulated by toxins, the initial potential is 0.2 V, and the frequency range is 1 Hz-$10^5$ Hz.

In an embodiment of the disclosure, the electrochemical AC impedance method (EIS) measures the signals obtained by the electrochemical sensor stimulated by different concentrations of toxins, the impedance value is calculated by fitting the equivalent circuit with Zview software, the cell viability inhibition rates of different concentrations of toxins are calculated, and the calculation method is as follows:

$$\text{Inhibition rate } (\%) = \left(1 - \frac{R_{dosing} - R_{carbon\ nanofiber/GelMA}}{R_{0dosing} - R_{carbon\ nanofiber/GelMA}}\right) \times 100$$

wherein $R_{dosing}$ refers to the impedance value of the screen-printed carbon electrode (SPE) with toxin stimulation and bioprinting modification, $R_{0dosing}$ refers to the impedance value of the screen-printed carbon electrode (SPE) with bioprinting modification and without toxin stimulation, and $R_{carbon\ nanofiber/GelMA}$ refers to the impedance value of the SPE with modification of carbon nanofibers and GelMA hydrogel and without cells.

In an embodiment of the disclosure, a combined effect formula in the combination index method is:

$$\frac{f_a}{f_u} = \left(\frac{D}{D_m}\right)^m$$

wherein $f_a$ refers to a cell damage effect rate, f refers to a cell undamaged effect rate, D refers to a toxin concentration, $D_m$ refers to a toxin concentration when the cell damage effect rate reaches 50%, and m refers to a dose-effect curve coefficient.

In an embodiment of the disclosure, a calculation formula of the CI index of the combination index method is:

$$CI_x = \sum_{j=1}^{n} \frac{(D)_j}{(D_x)_j}$$

wherein $(D)_j$ refers to the required concentration when x % damage effect is caused by the combined effect of toxins, $(D_x)_j$ refers to the concentration when x % damage effect is caused by a single toxin, and if CI>0.9, the combined effect type of toxins is considered to be antagonism; if CI=0.9-1, the combined effect type of toxins is considered to be an additive effect; and if CI<0.9, the combined effect type of toxins is considered to be synergism.

The fourth objective of the disclosure is application of the cell electrochemical sensor in the fields of drug development, toxicology testing and environmental monitoring.

Compared with the prior art, the disclosure has the following advantages:

(1) In the disclosure, carbon nanofibers are added into GeMA to improve the conductivity of the hydrogel, so that the prepared sensor has higher sensitivity for the detection of toxins.

(2) In the disclosure, the screen-printed carbon electrode is used as the sensing interface, the constructed cell sensor chip has the advantages of small size, portability, low sample requirement amount, high detection speed, mass production and modification and the like, and the problem of cross pollution in practical application is avoided.

(3) The cell sensor of the disclosure can be used for determining the toxic effect degrees of two or more deoxynivalenol-family mycotoxins. For a long time, China's food and feed have been seriously polluted by mycotoxins, and pollution caused by multiple toxins at the same time also happens. The disclosure can be used for not only determining the cytotoxicity of a single toxin and two or more toxins, but also further determining the combined effect type of the toxins, and references can be provided for the determination of relevant testing standards.

(4) In the disclosure, a three-dimensional cell culture system is constructed through reasonable combination of a 3D printing technology and the cell electrochemical sensing field. The method is convenient and reliable to operate, human errors are reduced to a certain extent, a new method and idea are provided for evaluating the toxicity of mycotoxins, a more realistic and effective evaluation method is also provided for the study of combination toxicity mechanisms, and the cell sensor is expected to be applied in the fields of food safety, biomedicine and the like.

BRIEF DESCRIPTION OF FIGURES

FIG. 3: Electrochemical characterization diagrams of a construction process of the cell electrochemical sensor, wherein in FIGS. 3A-3C, a refers to a bare electrode (SPCE), b refers to an electrode modified with AuNPs (AuNP/SPCE), c refers to a carbon nanofiber/GeMA/AuNPs electrode (CN/GelMA/AuNP/SPCE), and d refers to a cell/carbon nanofiber/GeMA/AuNPs electrode (cells/CN/GelMA/AuNP/SPCE).

FIG. 5: EIS detection result diagrams of the cell sensor when the cell electrochemical sensor is used for evaluating DON, 15-ADON and the combined effect of the two toxins, wherein

FIG. 6: Experimental comparison results of the cell electrochemical sensor and a CCK8 method in evaluating the cytotoxicity, wherein

FIG. 8.

FIG. 9.

DETAILED DESCRIPTION

The preferred examples of the disclosure will be described below. It should be understood that the examples are used for better explaining the disclosure and are not intended to limit the disclosure. The carbon nanofibers used in the following examples and comparative example are purchased from Xianfeng Nano, the model is XFM60, the diameter is 200-600 nm, and the length is 5-50 µm.

Example 1 Preparation of a Cell Electrochemical Sensor

Figure 2:
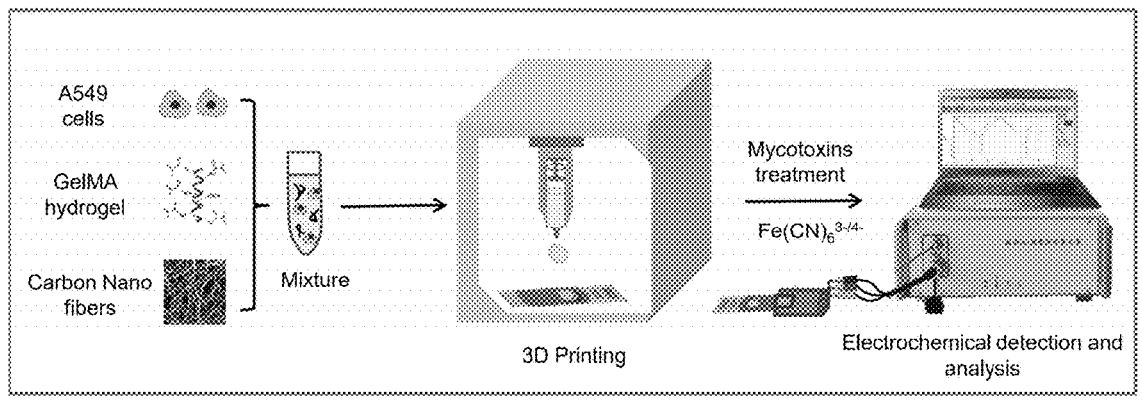
FIG. 2: A schematic diagram of a 3D printing process for preparing a cell electrochemical sensor.

A method for constructing a cell electrochemical sensor based on a 3D printing technology (shown as FIG. 2) comprises the following steps:

(1) Preparation of a gelatin methacryloyl (GelMA) solution: An LAP initiator is added into a DMEM cell culture medium to make the final concentration reach 0.5%, and then dissolving is carried out in a water bath at 60° C. for 30 min in the dark to obtain a dissolved standard initiator solution. A GelMA material is added into the dissolved standard initiator solution for dissolving in a water bath at 60° C. for 30 min in the dark, and shaking is carried out 3 times during the period to obtain a GelMA solution (the mass concentration is 7.5%); and then the obtained GeMA solution is filtered with a 0.22 m sterile filter membrane into a clean container for use.

(2) Preparation of a cell/carbon nanofiber/GelMA composite hydrogel: A certain amount of carbon nanofibers are added into a phosphate buffer solution (PBS) to make the concentration of carbon nanofibers reach 1 mg/mL, ultrasonic treatment is carried out for 2 hours, and then a prepared carbon nanofiber solution is placed under an ultraviolet light for irradiation overnight. A certain amount of the carbon nanofiber solution is added into the GeMA solution obtained by filtration in step (1), the mixed solution is thoroughly mixed to make the GeMA concentration reach 7.5% and the carbon nanofiber solid filling amount reach 0.05%, and a carbon nanofiber/GelMA composite solution is obtained. The human lung adenocarcinoma epithelial cells A549 are uniformly mixed with the carbon nanofiber/GelMA composite solution, and the cell concentration is adjusted to be $1 \times 10^6$/mL to obtain the cell/carbon nanofiber/GeMA composite hydrogel.

Figure 1:
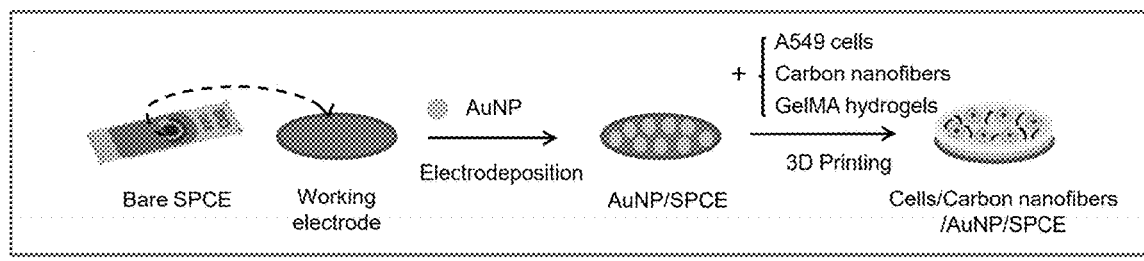
FIG. 1: A schematic diagram of the modification process of a screen-printed electrode.

(3) Modification and electroplating of a screen-printed carbon electrode with gold nanoparticles (shown as FIG. 1): The screen-printed carbon electrode needs to be activated in a 0.5 mmol/L sulfuric acid solution first and then scanned by cyclic voltammetry, the voltage is −0.2 V-0.6 V, the scanning rate is 100 mV/s, and the scanning circle number is 8. The activated screen-printed carbon electrode is immersed in a 10 mL of a gold electroplating solution containing 1% chloroauric acid and 1 mmol/L sulfuric acid solution, a time-current method is adopted, the electroplating voltage is −0.3 V, the electroplating time is 120 seconds, and then the electrode is rinsed with ultrapure water, dried with nitrogen and placed under an ultraviolet light overnight for irradiation and sterilization to obtain the screen-printed carbon electrode modified and electroplated with gold nanoparticles.

(4) 3D printing: The cell/carbon nanofiber/GelMA composite hydrogel prepared in step (2) is poured into a printing syringe, the syringe temperature is set to be 26° C., the working platform temperature is 3° C., the extrusion pressure is 0.1 MPa, the graphic length is 3 mm, the graphic width is 3 mm, the printing layer number is 1, the nozzle walking speed is 300 mm/min, the screen-printed carbon electrode modified and electroplated with gold nanoparticles prepared in step (3) is placed at a specific position on the working platform, a printing procedure is run to precisely deposit the composite hydrogel on the working electrode of the screen-printed carbon electrode, and the composite hydrogel is irradiated with a portable curing light source with the wavelength of 405 nm for 10-20 seconds for curing to obtain the cell electrochemical sensor.

The cell electrochemical sensor obtained in step (4) needs to undergo cell incubation before application, and specific steps comprise: dropping a 150 µL of the DMEM cell culture medium at the working electrode of the screen-printed carbon electrode to ensure that the culture medium can cover a cell/carbon nanofiber/GelMA complex on the working electrode to provide cells with nutrients needed for growth, and then placing the working electrode in an incubator with the carbon dioxide concentration of 5% and the humidity of 95% for incubation at 37° C. for 6 hours to obtain the incubated cell electrochemical sensor.

Cyclic voltammetry, differential pulse voltammetry, an AC impedance method and scanning electron microscope characterization are performed on the cell electrochemical sensor after incubation. The conditions of the voltammetry method are: the voltage of −0.2 V-0.6 V and the scanning rate of 100 mV/s; the condition of the AC impedance method is: the frequency range of 1 Hz-$10^5$ Hz. In the scanning electron microscope characterization, samples containing the cells A549 are tested after the cells are cultured in the CN/GeMA composite hydrogel for 48 hours.

Figure 3A:
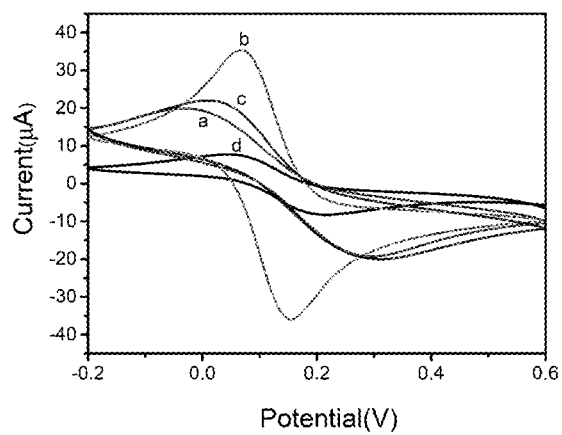
FIG. 3A is an electrochemical signal obtained by cyclic voltammetry (CV)
Figure 3B:
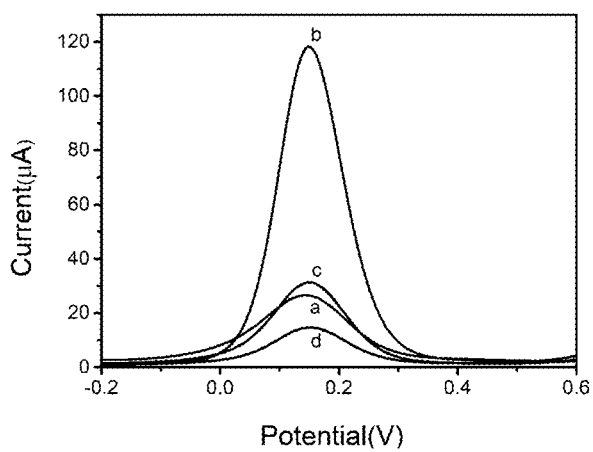
FIG. 3B is an electrochemical signal obtained by differential pulse voltammetry (DPV)
Figure 3C:
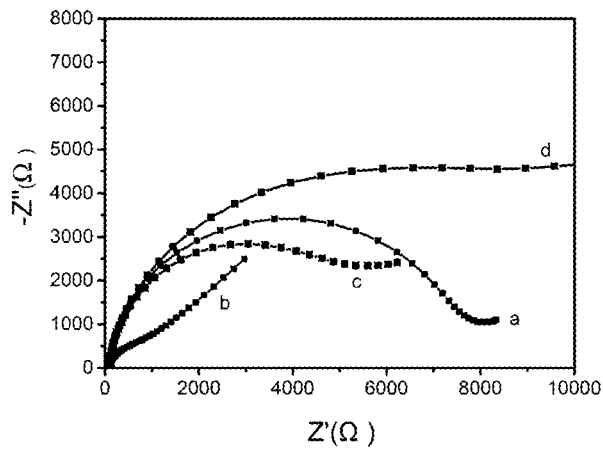
FIG. 3C is an electrochemical signal obtained by electrochemical impedance spectroscopy (EIS)

As shown in FIG. 3, compared with a bare screen-printed carbon electrode, the electrical signal of the gold-plated screen-printed carbon electrode is significantly enhanced, and it is indicated that the gold nanoparticles have excellent conductivity. When the carbon nanofiber/GelMA hydrogel is deposited on the working electrode, the electrical signal is reduced to some extent. When the cell/carbon nanofiber/GelMA hydrogel is deposited on the working electrode, the electrical signal is further reduced due to the insulation of cell membranes, it is indicated that the cells are successfully modified on the electrode surface, and preparation of the cell electrochemical sensor is completed.

Figure 4A:
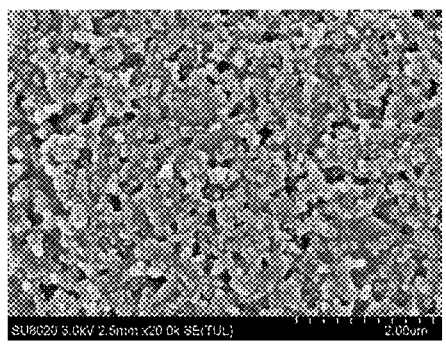
FIG. 4 is electrode-modified electron microscope characterization diagrams, wherein FIG. 4A refers to a bare electrode (SPCE)
FIG. 4B refers to an electrode modified with AuNPs (AuNP/SPCE-modified electrode)
FIG. 4C refers to a cell/carbon nanofiber/GeMA/AuNPs electrode (cells/CN/GelMA/AuNP/SPCE-modified electrode)
FIG. 4D refers to cells growing in clusters in a cell/carbon nanofiber/GeMA composite hydrogel.
Figure 4B:
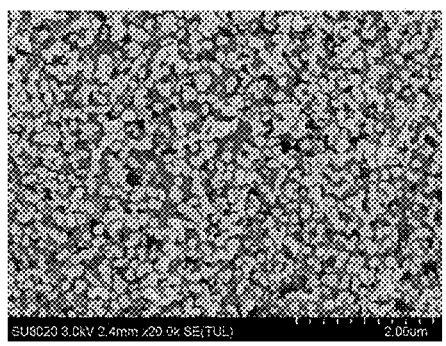
Figure 4C:
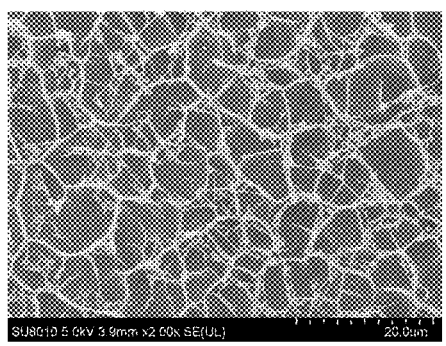
Figure 4D:
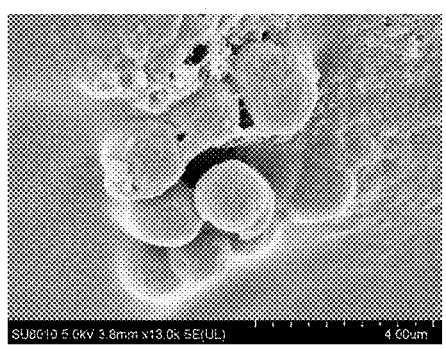
Figure 5A:
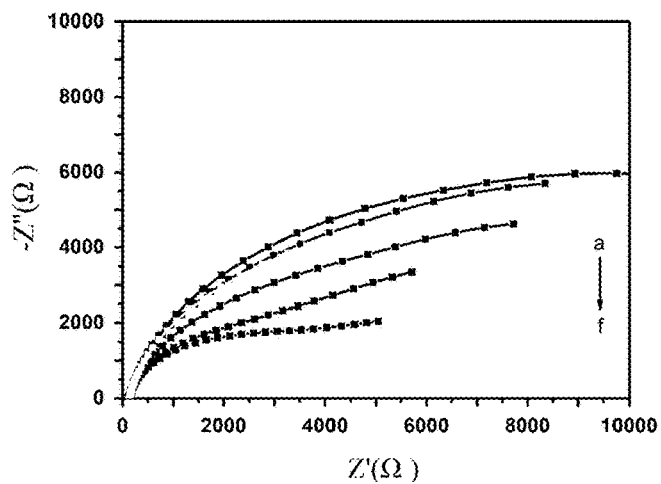
FIG. 5A is an EIS detection result diagram of the cell sensor after 24 hours of DON stimulation, and a-f refer to the toxin concentrations of 0.1, 0.2, 0.5, 1, 2 and 5 µg/mL respectively.
Figure 5B:
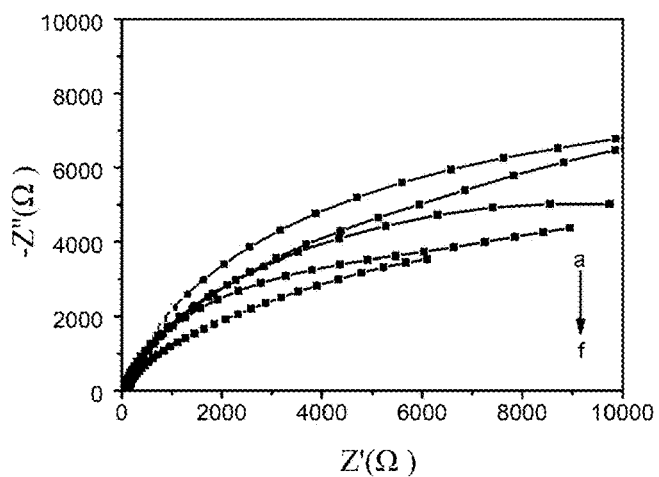
FIG. 5B is an EIS detection result diagram of the cell sensor after 24 hours of 15-ADON stimulation, and a-f refer to the toxin concentrations of 0.1, 0.2, 0.5, 1, 2 and 5 µg/mL respectively.
Figure 5C:
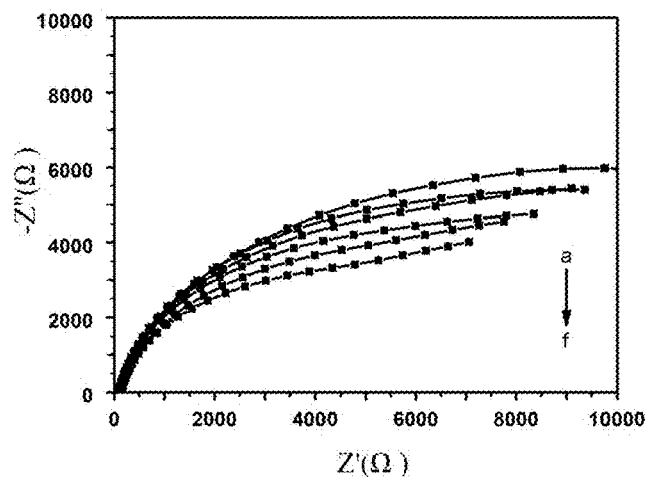
FIG. 5C is an EIS detection result diagram of the cell sensor after 24 hours of DON and 15-ADON stimulation, and a-f refer to the toxin concentrations of 0.1+0.1, 0.2+0.2, 0.5+0.5, 1+1, 2+2 and 5+5 µg/mL respectively.
Figure 5D:
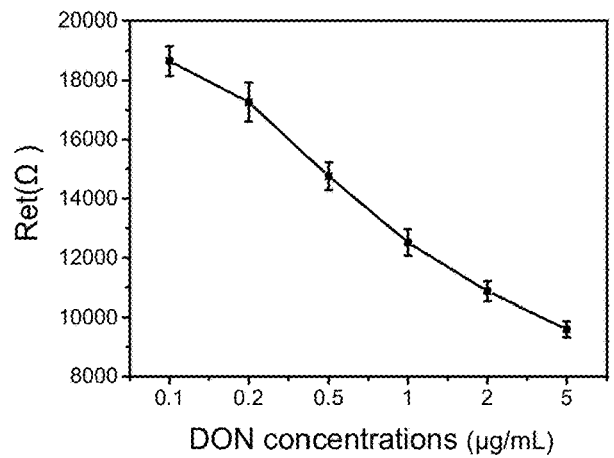
FIG. 5D is a correlation curve of different concentrations of DON and the electrochemical impedance value of the constructed sensor.
Figure 5E:
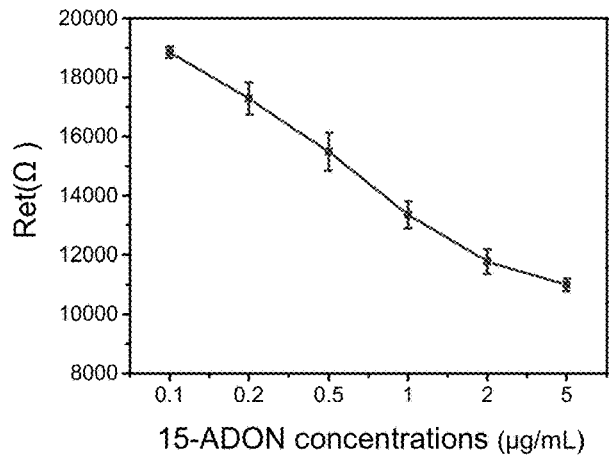
FIG. 5E is a correlation curve of different concentrations of 15-ADON and the electrochemical impedance value of the constructed sensor.
Figure 5F:
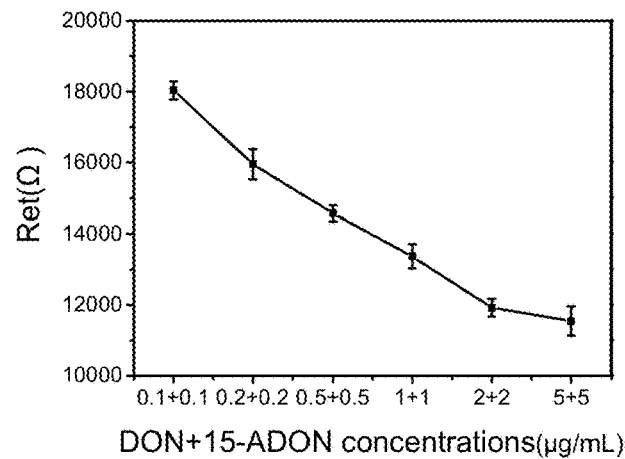
FIG. 5F is a correlation curve of different concentrations of DON+15-ADON and the electrochemical impedance value of the constructed sensor.

The electrode-modified electron microscope characterization diagram in FIG. 4 shows that AuNPs are evenly distributed on the electrode surface (FIG. 4B). FIG. 4C shows uniform immobilization of carbon nanofibers in the GeMA hydrogel, which increases catalytically active sites for achieving better electrochemical performance. After the cells A549 are introduced into the screen-printed carbon electrode, the cells are firmly immobilized and evenly distributed in the CN/GelMA composite hydrogel. In addition, the cells are also aggregated in the composite hydrogel, which maintain complete cell morphologies (FIG. 4D), the good physical state of the cells in the hydrogel is confirmed, and redox probes are prevented from entering the electrode surface, so that the electron transfer resistance is increased.

Example 2 Application of a Cell Electrochemical Sensor Based on a 3D Printing Technology The incubated electrochemical sensor obtained in example 1 is used for evaluating the cytotoxicity of deoxynivalenol-family mycotoxins, and specific operations are as follows:

(1) Drug stimulation: An original culture medium on a working electrode is removed, toxin standard substances are diluted with a DMEM cell culture medium into gradient concentration solutions, and then 150 μL of DON toxin solutions in the concentration range of 0.1, 0.2, 0.5, 1, 2 and 5 μg/mL, 150 μL of 15-ADON toxin solutions in the concentration range of 0.1, 0.2, 0.5, 1, 2 and 5 μg/mL and 150 μL of DON+15-ADON toxin solutions in the concentration range of 0.1+0.1, 0.2+0.2, 0.5+0.5, 1+1, 2+2 and 5+5 μg/mL are taken and dropped on the working electrode printed with cells respectively, the working electrode is placed in an incubator for effect for 24 hours, and corresponding impedance values are measured.

(2) Detection of electrochemical signal values: A 150 μL of 2.5 mM $Fe(CN)_6^{3-/4-}$ PBS solution is used as an electrode reaction system, the frequency range of an electrochemical AC impedance method (EIS) is 1 Hz-$10^5$ Hz, and the impedance value is fitted by Zview software and calculated through the best equivalent circuit. The toxic effects on cells are generated after different doses of toxins stimulate the cells, EIS is used for analyzing the toxicity of the toxins on the lung adenocarcinoma epithelial cells A549, and a calculation method is as follows:

$$\text{Inhibition rate (\%)} = \left(1 - \frac{R_{dosing} - R_{carbon\ nanofiber/GelMA}}{R_{0dosing} - R_{carbon\ nanofiber/GelMA}}\right) \times 100$$

wherein $R_{dosing}$ refers to the impedance value of the screen-printed carbon electrode (SPE) with toxin stimulation and bioprinting modification, $R_{0dosing}$ refers to the impedance value of the screen-printed carbon electrode (SPE) with bioprinting modification and without toxin stimulation, and $R_{carbon\ nanofiber/GelMA}$ refers to the impedance value of the SPE with modification of carbon nanofibers and GelMA hydrogel and without cells.

The combined effect type can be determined by substituting the inhibition rate obtained after the sensor is stimulated by toxins into a combination index formula, and a combined effect formula in the combination index method is:

$$\frac{f_a}{f_u} = \left(\frac{D}{D_m}\right)^m$$

wherein $f_a$ refers to a cell damage effect rate, $f_u$ refers to a cell undamaged effect rate, D refers to a toxin concentration, $D_m$ refers to a toxin concentration when the cell damage effect rate reaches 50%, and m refers to a dose-effect curve coefficient.

A calculation formula of the CI index is:

$$CI_x = \sum_{j=1}^{n} \frac{(D)_j}{(D_x)_j}$$

wherein $(D)_j$ refers to the required concentration when x % damage effect is caused by the combined effect of toxins, $(D_x)_j$ refers to the concentration when x % damage effect is caused by a single toxin, and if CI>0.9, the combined effect type of toxins is considered to be antagonism; if CI=0.9-1, the combined effect type of toxins is considered to be an additive effect; and if CI<0.9, the combined effect type of toxins is considered to be synergism.

(3) Result judgment

TABLE 1

CI index values obtained after analysis of the combined effect of mycotoxins by the cell electrochemical sensor

| Concentration of mycotoxins/(μg/mL) | | Inhibition rate/100 | | Combined |
|---|---|---|---|---|
| DON | 15-ADON | $f_a$ | CI | effect type |
| 0.1 | 0.1 | 0.0877 | 1.23033 | Antagonism |
| 0.2 | 0.2 | 0.2768 | 0.80967 | Synergism |
| 0.5 | 0.5 | 0.4027 | 1.28417 | Antagonism |
| 1 | 1 | 0.5122 | 1.79919 | Antagonism |
| 2 | 2 | 0.6426 | 2.33635 | Antagonism |
| 5 | 5 | 0.6778 | 5.14921 | Antagonism |

As shown in FIG. 5, the impedance value of the cell sensor prepared in example 1 is gradually reduced with the increasing dose of DON in the concentration range of 0.1-5 μg/mL and the increasing dose of 15-ADON in the concentration range of 0.1-5 μg/mL, the reason is that after different doses of toxins stimulate the cells A549, the cells can undergo different degrees of apoptosis, lysis, and morphological changes, and thus changes of impedance electrochemical signals are caused. The $IC_{50}$ value of DON measured by the EIS method is 0.9281 μg/mL, the $IC_{50}$ value of 15-ADON is 1.2560 μg/mL, the $IC_{50}$ value of DON and 15-ADON during combined effect is 2.279 μg/mL, and specific results are shown in Table 1. It is found by using the cell electrochemical sensor constructed in example 1 to analyze the combined effect type of DON and an acetylated derivative 15-ADON thereof that the two toxins generally show an antagonistic effect.

Example 3 A Verification Experiment

The CCK8 method is used for detecting the cytotoxicity of DON, 15-ADON and DON+15-ADON alone and in combination. The lung adenocarcinoma epithelial cells A549 with the density of $5\times10^4$/mL are adhered to the wall of a 96-well plate for inoculation, a culture medium is removed after culture for 24 hours, and 100 μL of the toxin solution same as that in example 2 is added. After 24 hours of toxin stimulation, the supernatant is sucked out, a 100 μL of culture medium containing 10% CCK8 is added into each well for incubation at 37° C. for 2 hours, then the absorbance value is measured with a microplate reader at 450 nm, the cell activity inhibition rate is calculated, and the calculation method is as follows:

$$\text{Inhibition rate (\%)} = \left(1 - \frac{OD_{dosing} - OD_{blank}}{OD_{0dosing} - OD_{blank}}\right) \times 100$$

wherein $OD_{dosing}$ refers to the absorbance value after 24 hours of toxin stimulation, $OD_{0dosing}$ refers to the absorbance value after 24 hours of toxin-free stimulation, and $OD_{blank}$ refers to the absorbance value of the pure cell culture medium.

Figure 6A:
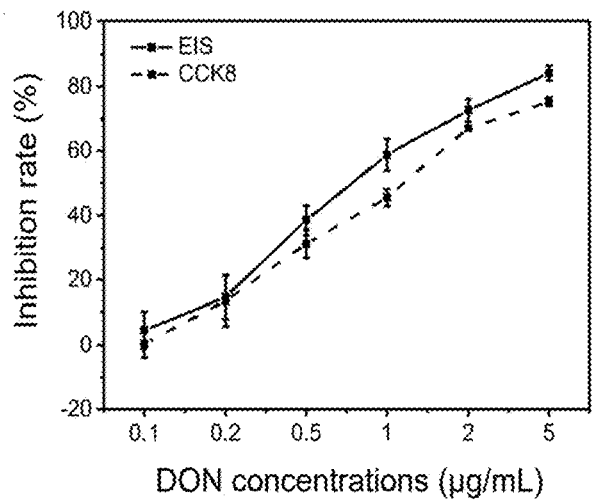
FIG. 6A is DON.
Figure 6B:
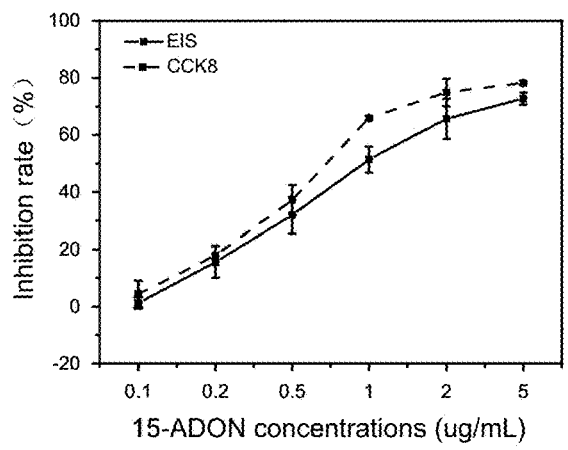
FIG. 6B is 15-ADON.
Figure 6C:
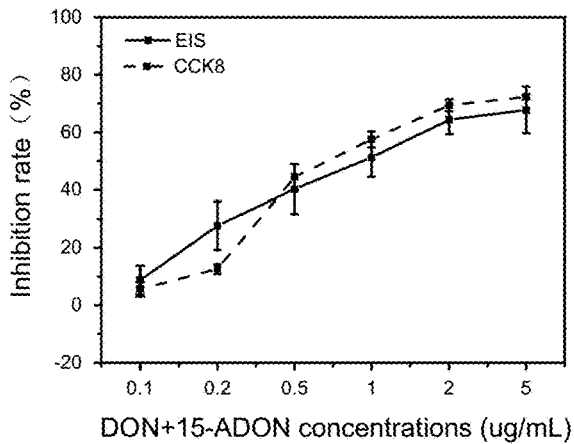
FIG. 6C is the combined effect of the two toxins DON and 15-ADON.

It can be seen from FIG. 6 that the measurement structure of the cell electrochemical sensor constructed in example 1 for evaluating the cytotoxicity of vomitoxin is in good consistency with the results measured by a traditional cytotoxicology method, and the cell electrochemical sensor can be used for effectively determining the cytotoxicity of toxins.

Example 4 Optimization of Preparation Parameters of the Cell/Carbon Nanofiber/GeMA Composite Hydrogel (1) Final Concentration of Cells According to example 1, a series of gradient cell concentrations of cell/carbon nanofiber/GelMA hydrogels are prepared to make the final concentrations of the lung adenocarcinoma epithelial cells A549 reach $1\times10^3$/mL, $1\times10^4$/mL, $1\times10^5$/mL, $1\times10^6$/mL and $1\times10^7$/mL respectively, other parameters remain unchanged, then the cell/carbon nanofiber/GeMA hydrogels are deposited on the gold-plated screen-printed carbon electrode through 3D printing to obtain different cell concentrations of electrochemical sensors, and electrochemical signals are tested by an AC impedance method.

Figure 7:
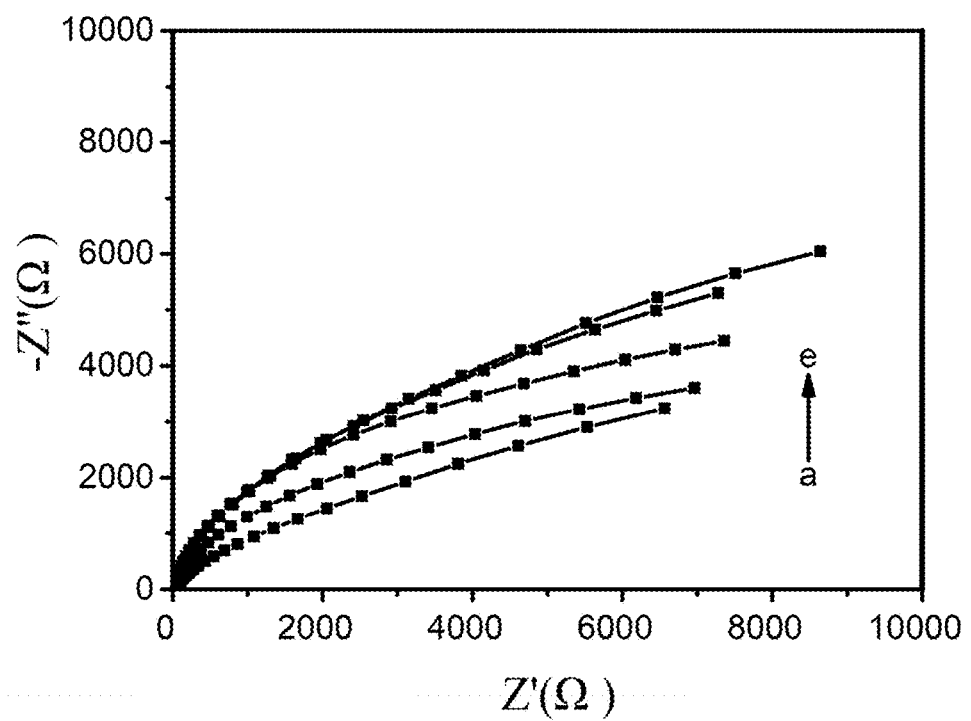
FIG. 7: An impedance spectrum diagram of electrochemical sensors prepared with different concentrations of the lung adenocarcinoma epithelial cells A549, wherein the cell concentration ranges of a-e are $1 \times 10^3$/mL, $1 \times 10^4$/mL, $1 \times 10^5$/mL, $1 \times 10^6$/mL and $1 \times 10^7$/mL respectively.

As shown in FIG. 7, as the cell concentration is increased, the blocking effect of cell membranes on the current is improved, and the impedance value of the cell electrochemical sensor is increased. When the cell concentration reaches $1\times10^6$/mL-$1\times10^7$/mL, the impedance value is no longer increased significantly, it is indicated that the cells on the electrode surface are saturated at this time, and the formed cell electrochemical sensor stays in a relatively stable state. Therefore, the cell concentration range of $1\times10^6$/mL-$1\times10^7$/mL is adopted.

(2) Final Concentration of GeMA

According to example 1, the final GeMA concentrations are adjusted to 5%, 7.5%, 10%, 12.5% and 15% respectively to prepare cell/GelMA hydrogels, then the cell/GelMA hydrogels are deposited on the gold-plated screen-printed carbon electrode through 3D printing, a calcein-AM/PI cell live and dead double staining kit is used for detecting the cell viability of cells incubated in different concentrations of GelMA hydrogels for 72 hours, and differential pulse voltammetry is used for testing the electrochemical signals.

A cell live and dead staining experiment is carried out according to instructions of the kit: the cell/GelMA hydrogel is observed under a laser confocal microscope after staining, and yellow-green fluorescent live cells and red fluorescent dead cells are observed at the same time at an excitation wavelength of 490±10 nm. In addition, the dead cells are observed separately at an excitation wavelength of 545 nm, and then cell viability statistics is carried out through a counting function of an instrument.

Figure 8A:
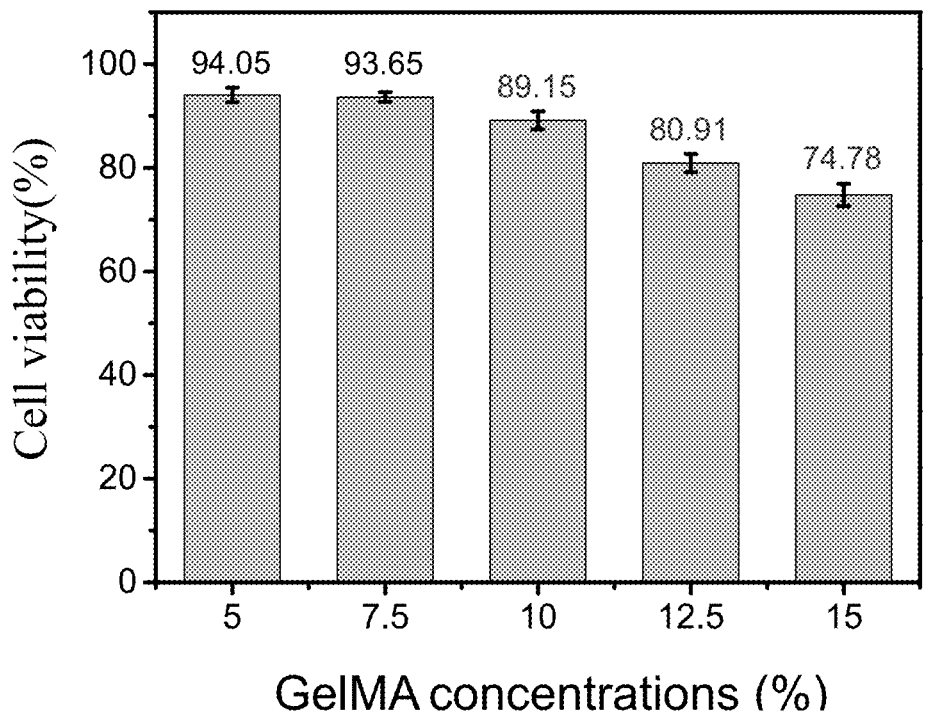
FIG. 8A refers to the survival rate of the lung adenocarcinoma epithelial cells A549 in different concentrations of GelMA hydrogels.
Figure 8B:
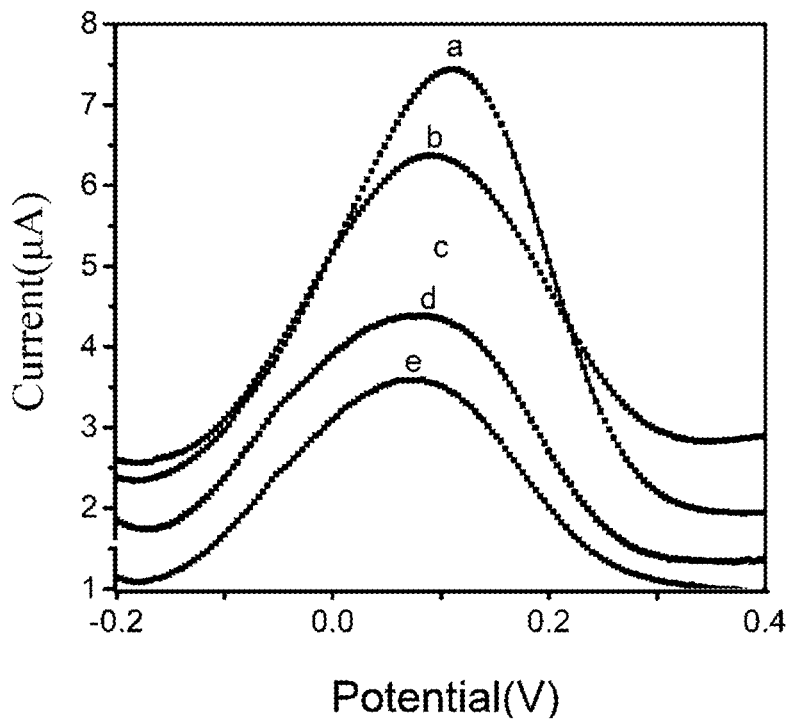
FIG. 8B is a DPV detection result diagram of the electrode when different concentrations of GelMA hydrogels are printed on the screen-printed carbon electrode, wherein a-e refer to the GeMA concentrations of 5%, 7.5%, 10%, 12.5% and 15% respectively.

As shown in FIG. 8A, the cells A549 have a high survival rate in the GeMA concentration range of 5-7.5%. It can be seen from FIG. 8B that as the concentration of GeMA is increased, the current value of the screen-printed carbon electrode is reduced, the impedance value is increased, and in order to ensure the activity of the cells in the sensor and the sensitivity of the sensor, the GelMA concentration range of 5-7.5% is adopted. If the GeMA concentration is too low, the requirements of 3D printing cannot be met.

Comparative Example 1

The 3D printing method of example 1 is adjusted to a dropping method, that is to say, a 10 μL of cell/carbon nanofiber/GelMA hydrogel is taken and dropped on the screen-printed working electrode through a pipette, other parameters remained unchanged, and the cell electrochemical sensor is prepared.

Figure 9A:
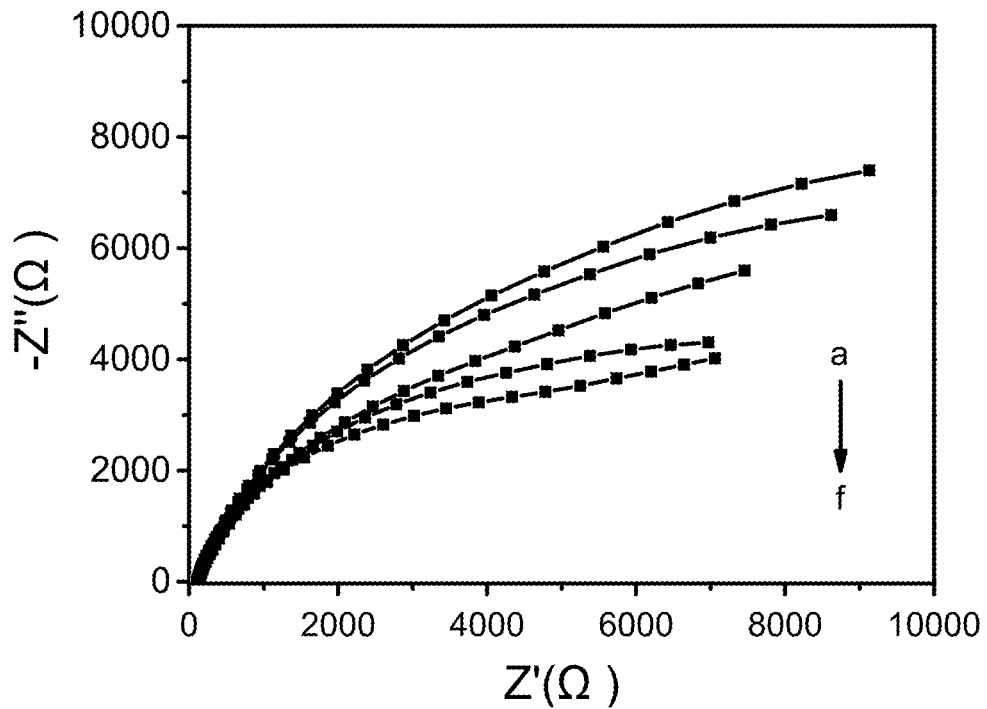
FIG. 9A is an EIS detection result diagram of the cell sensor when the DON toxin stimulates the cell electrochemical sensor prepared by a dropping method, wherein a-f refer to the DON toxin concentrations of 0.1, 0.5, 2, 0.2, 1 and 5 µg/mL respectively.
Figure 9B:
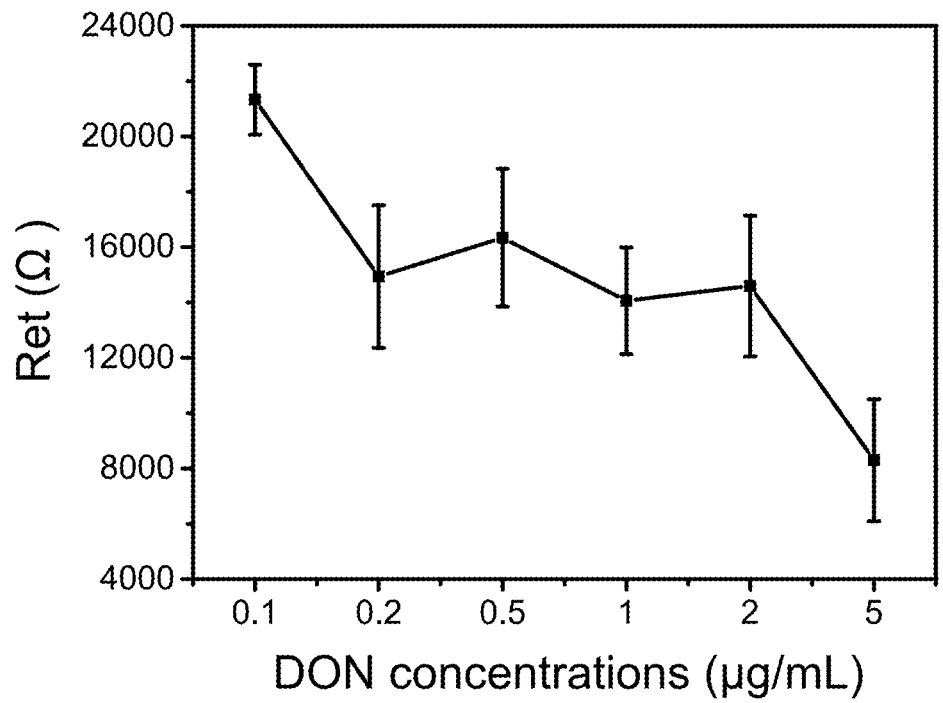
FIG. 9B is a correlation curve graph of the DON toxin and the sensor impedance value.

The prepared cell electrochemical sensor is used for electrochemical detection of DON cell toxicity, and results of EIS detection and impedance value changing with toxin concentrations are shown as FIG. 9. It can be seen that there is no regular linear relationship between the dose of the DON toxin and the impedance value of the cell electrochemical sensor, and there are large errors between parallel dose groups. It is indicated that the deposition of the cells, carbon nanofibers and hydrogel on the screen-printed carbon electrode in a dropping method can cause the problem of uneven distribution of cells and materials due to human errors, thereby reducing the detection precision.

Therefore, the 3D printing method can be used for more precisely positioning biological materials and living cells, human errors are reduced to a certain extent, mass production is allowed, and the method has the advantages of ensuring the precision and being convenient in operation.

What is claimed is:

1. A method for making a cell electrochemical sensor, wherein the method is based on a 3D printing technology comprising the following steps:
    preparing a cell/carbon nanofiber/gelatin methacryloyl (GelMA) composite hydrogel by mixing a carbon nanofiber solution with a GelMA solution to obtain a carbon nanofiber/GelMA composite solution, and then uniformly mixing cells with the carbon nanofiber/GelMA composite solution to obtain the cell/carbon nanofiber/GelMA composite hydrogel; and
    depositing the cell/carbon nanofiber/GelMA composite hydrogel obtained on a working electrode of a screen-printed carbon electrode by 3D printing, and followed by curing to obtain the cell electrochemical sensor;
    wherein a final concentration of GelMA in the cell/carbon nanofiber/GelMA composite hydrogel is 5% to 15%;
    wherein a final concentration of cells in the cell/carbon nanofiber/GelMA composite hydrogel is $1\times10^6$/mL to $1\times10^7$/mL; and
    wherein the cells are lung adenocarcinoma epithelial cells A549.

2. The method of claim 1, wherein the screen-printed carbon electrode is coated with gold nanoparticles, and wherein the method further comprises irradiating the coated screen-printed carbon electrode and carbon nanofibers with ultraviolet light prior to depositing the cell/carbon nanofiber/GelMA composite hydrogel obtained on the working electrode of the screen-printed carbon electrode.

3. The method of claim 1, wherein the screen-printed carbon electrode is printed on PET as a substrate.

4. The method of claim 1, wherein the screen-printed carbon electrode is a circle with the diameter of 3 mm and a printing layer height of 0.3 mm.

5. The method of claim 1, wherein curing comprises irradiation of the cell electrochemical sensor with light source comprising a wavelength of 405 nm.

6. The method of claim 1, wherein preparing the cell/carbon nanofiber/gelatin methacryloyl (GelMA) composite hydrogel further comprises adding lithium phenyl-2,4,6-trimethylbenzoylphosphinate (LAP), GelMA, and carbon nanofiber to a cell culture medium to form the carbon nanofiber/GelMA composite solution, and then adding the cells to the carbon fiber/GelMA composite solution to obtain the cell/carbon nanofiber/GelMA composite hydrogel.

* * * * *